United States Patent [19]
Morse et al.

[11] 4,123,382
[45] Oct. 31, 1978

[54] METHOD OF MICROENCAPSULATION

[75] Inventors: Lewis D. Morse, Princeton; William G. Walker, Avenel; Paul A. Hammes, Westfield, all of N.J.

[73] Assignee: Merck & Co., Inc., Rahway, N.J.

[21] Appl. No.: 364,223

[22] Filed: May 25, 1973

[51] Int. Cl.² .......................... B01J 13/02; A61K 9/50
[52] U.S. Cl. ...................................... 252/316; 424/34; 424/35; 424/37; 424/252; 424/274; 424/280; 424/310; 427/3; 427/212
[58] Field of Search .......................... 252/316; 424/35; 117/100 A; 427/3, 212

[56] References Cited

U.S. PATENT DOCUMENTS

| | | | |
|---|---|---|---|
| 2,911,338 | 11/1959 | Tabern et al. | 424/1 |
| 3,415,758 | 12/1968 | Powell et al. | 252/316 |

*Primary Examiner*—Richard D. Lovering
*Attorney, Agent, or Firm*—Frank M. Mahon; John Frederick Gerkens; Harry E. Westlake, Jr.

[57] ABSTRACT

Solids are added to a suspension of heat softened ethylcellulose capsules and are then encapsulated within the soft capsule. Cooling permits recovery of the desired encapsulated product.

6 Claims, No Drawings

METHOD OF MICROENCAPSULATION

This invention relates to an improved method of obtaining microencapsulated products. More specifically, it relates to a method of microencapsulation in which the solid to be encapsulated is added to a suspension of heat softened blank capsules and, after the solid had penetrated the blank capsules, microencapsulated product is recovered. Still more specifically, this invention relates to a method for obtaining improved control of microencapsulation size, improved bioavailability, and increased production of microencapsulated product by first preparing blank microcapsules, then heat softening them and adding the solid core.

BACKGROUND OF THE INVENTION

In known processes for microencapsulation, there are produced cores of encapsulated material surrounded by continuous shells of solid encapsulating material. These are usually performed by suspending the core material in a solvent and depositing the shell in liquid form from the solvent on the core. Liquid shell is then converted to a rigid solid shell. For example, many solids have been encapsulated with ethylcellulose by suspension of the solids in a cyclohexane solution of ethylcellulose containing another polymer such as polyethylene at a temperature of 80° C. Cooling the solution forms minute droplets of ethylcellulose which enveloped the solid particles. Further cooling gives capsules of minute size having the solid encapsulated in ethyhlcellulose, and these can be recovered and dried by methods known in the art.

There are two broad types of microencapsulated products, in terms of particle size of the internal phase (the material being encapsulated): 1. Relatively large materials, 250 microns across, or even as small as 75 to 100 microns, are usually enrobed individually. 2. Very small materials, less than a micron to 10 or 20 microns, are usually enrobed as aggregates. That is, the enrobing polymer gathers scores or hundreds of particles within a single microcapsule.

Examination of microcapsules of the first type at as low as 40X magnification shows a clearly defined wall, of 2 to 50 microns, depending on the amount of polymer used. Examination of microcapsules of the second type at as high as 1,000X magnification shows a barely discernible wall, in some cases indiscernible. Such walls range from 1 or 2 microns thick, down to hundredths or thousandths of a micron.

The distinguishing feature between microcapsules of type 1 and type 2 is the distribution of wall or polymer material. In the first type, the wall material is distributed on the periphery of single particles. In the second type the polymer is distributed throughout the microcapsule, as well as on the periphery of the capsule. The tremendous surface area within the microcapsule, provided by the aggregation of minute particles, leaves very little polymer for the periphery.

One of the disadvantages of the prior art is that it is difficult to control the size of the microcapsule since the stirring rate needed to disperse the solid core causes the formation of very small capsules. This invention, where it concerns particle size control, has to do with microcapsules of the second type.

The rates of stirring required to disperse the internal phase are such that very small capsules generally result. There is an equilibrium of aggregation and dispersion of the material being stirred and distributed in the solvent. This equilibrium is pushed in the direction of dispersion due to the required high stirring rate. The rate that is thus required will yield correspondingly small microcapsules.

Another disadvantage of the prior art is that it is difficult to obtain good bioavailability of moderately water soluble solids. There is no problem in respect to bioavailability of highly water soluble internal phases. Gastric or intestinal fluid diffuses through the microcapsule wall and dissolves internal phase material. The resultant solution diffuses from the microcapsule to the gastrointestinal tract. The diffusion in each direction continues over a period of time until essentially all of the internal phase is released. Sparingly soluble substances present a problem in this context, since only small quantities of dissolved material diffuse from the microcapsule into the gastrointestinal tract.

A still further disadvantage of the known method is that productivity of microcapsules per batch is limited by the amount of solids that can be dissolved and dispersed in the continuous liquid phase in which the preparation takes place.

THE INVENTION

We have found that excellent results are obtained when blank capsules are prepared and heat softened, followed by addition of the solid to be encapsulated. The mixture is then stirred until the solid is encapsulated in the blanks, after which the microcapsules are solidified and recovered.

It is an object of this invention to improve the control of the size of the microcapsules.

It is a still further object of this invention to increase the release rate or bioavailability of the encapsulated material.

A still further object of this invention is to improve the productivity in the preparation of microcapsules.

The above objects are accomplished by: 1. Preparing "empty" microcapsules, softening them, and "filling" them, or 2. Preparing microcapsules, complete with internal phase, softening them, and adding internal phase to "fill" the capsules further. The fundamental principle here is that coating polymer can be phased out of solution before internal phase is added to the system. If internal phase is added while the coating polymer is plastic, the internal phase enters the polymer and is enrobed.

The advantages of our invention are that:

1. Particle size can be controlled. The impeller RPM can be adjusted so that large or small plastic polymer masses develop. The size of these masses influences the final microcapsule size. This is in contrast to traditional microencapsulation where the rates of stirring required to disperse the internal phase are such that very small capsules result.

2. Bioavailability of moderately water soluble substances can be increased. This is accomplished by introducing the material to be encapsulated at a temperature where the polymer masses are only moderately plastic. The internal phase under such conditions penetrates the polymer mass only partially. That is to say, only some of the internal phase gets to core of the mass; some stays inside the mass, near the periphery; a small amount is partially in the mass.

3. Productivity of microcapsules per batch can be increased. Since dissolved polymer is phased out of solution before the internal phase is added, a high total solids can be added to the solvent without reaching the limiting viscosity, or drag on the impeller, or loss in fluidity, that would be attained if the internal phase were dispersed in polymer solution.

4. Encapsulated materials can be formed chemically in situ inside the microcapsules by encapsulating first one reagent and then another. When these reagents come into contact upon becoming encapsulated, they can react to give a desired product. For example, an amine and an acid can be separately added to give a microencapsulated amine salt. Necessarily, neither the reagents by themselves nor any by-product may have otherwise undesirable properties (such as toxicity when the microcapsules are to be used in food or medicine).

5. For a given amount of wall material, by weight, the resultant wall is thicker.

While mention has been made above to use of ethylcellulose as the encapsulating material, this invention is not limited to such. Other well-known encapsulating materials such as methylcellulose, hydroxypropylmethylcellulose, polyvinyl alcohol, cellulose acetate phthallate, gelatin, gum arabic, carageenan alginates and the like can also be used. The preferred materials are ethylcellulose, methylcellulose, hydroxypropylmethylcellulose and gelatin.

The solid core to be inserted in the blank capsules in the process of this invention can be any food or medicinal material normally used in microcapsules. Among them can be mentioned reduced iron, iron salts, food acidulants, crystalline inorganic alkalis, other nutrients, aspirin, phenylephrine, epinephrine, chlortrimethon, antihistamines, antitussives, laxatives such as magnesium salts, antibiotics such as penicillin, diuretics, viruses, bacteria, enzymes—in short, any solid particulate matter.

The process of this invention can be run in any medium in which the blank capsules and the solid core are both insoluble, such as water, toluene, acetone, other hydrocarbons (hexane, etc.), and the like. In general, the continuous phase in the microencapsulating process should be one in which the solid core material is not soluble. Also, the encapsulating material should not be soluble in the continuous phase at the conditions used to soften it for use in this invention. However, the continuous phase could be a saturated solution of the encapsulating material at that temperature. The solid core material may, however, be soluble in the encapsulating material.

The blank capsule can be prepared by any method known in the art of microencapsulation. The phase inducing polymer can be polyethylene, butyl rubber, dextran, etc. The encapsulating material can be phased out by inorganic salts, etc. Phasing out of the encapsulating material can also be effected by cooling a solution under agitation. Alternatively, a non-solvent can be introduced into the system to phase out a polymer. The solid core material can be added right after the encapsulating material has been phased out of solution and is still soft, after which more solvent can be added to phase out more encapsulating material. Alternatively, blank capsules can be prepared in advance and stockpiled for later use and even sorted by screening into near uniform size. Such stock-blank capsules can then be reslurried in a suitable medium and softened (e.g. by heating), after which the solid core material is added.

Alternatively, a solid mass of encapsulating material can be slurried in a liquid medium in which it is not soluble, held at temperatures sufficiently elevated to soften it, and converted to blank microcapsules by vigorous agitation. An example of such would be a hot slurry of gelatin in cyclohexane.

The hardening of the filled capsule, in the process of this invention, can be carried out in any way known in the microencapsulation art. Since the softening process in many cases is thermal—the capsules are produced at elevated temperatures or softened by heating up a slurry—the hardening is achieved by cooling. In some cases, it can be effected by chemical reaction on the surface of the soft microcapsules. E.g. an aqueous sodium alginate solution is dispersed in a non-aqueous solvent such as cyclohexane or carbon tetrachloride. Droplets of aqueous sodium alginate are formed. Reduced iron particles, niacinamide or other particulate matter is then added and enters the spheres. Aqueous calcium chloride solution is then added. This is dispersed as droplets. The aqueous calcium chloride solution droplets go to the interface of the alginate/organic solvent system. Some enter the aqueous alginate spheres and some remain at the interface. In any case, calcium ions react with the sodium alginate, converting it to the insoluble calcium alginate, yielding microcapsules.

EXAMPLE I

A dispersion of 216 g. of ethylcellulose (47.5% ethoxyl content by weight, viscosity 45 cps at 25° C. as a 5% by weight solution in an 80:20 toluene:ethanol mixture) in 5 liters of cyclohexane is stirred using a downthrust turbine impeller and baffles operating at 310 RPM with heating. At 80° C. the ethylcellulose dissolves in the cyclohexane and stirring is continued while the system is allowed to cool. As the temperature drops, solvated ethylcellulose develops as a separate phase due to its lowered solubility in the cyclohexane. As the temperature drops further, the ethylcellulose loses solvent and develops into semiplastic, dispersed, small masses. At 50° C. the cooling is discontinued and 1088 g. of crystalline riboflavin is added. Microscopic examination of the small masses of ethylcellulose shows that it is plastic enough for most of the riboflavin to enter the masses and be enveloped. The temperature is raised to 57° C. and from a microscopic examination it is apparent that the riboflavin is enveloped. The mixture is then cooled to 10° C. and filtered. The solids are washed twice with 1.5 liters of hexane and dried in a fluid bed dryer to afford free flowing discrete microcapsules containing the riboflavin. These microcapsules have the following size distribution:

| Mesh | % by Weight |
| --- | --- |
| On 12 | 0.1 |
| −12/+16 | 0.1 |
| −16/+20 | 0.4 |
| −20/+30 | 0.6 |
| −30/+40 | 0.8 |
| −40/+60 | 1.3 |
| −60/+80 | 18.6 |
| −80/+100 | 31.4 |
| −100/+140 | 14.4 |
| −140/+200 | 23.6 |
| −200/+325 | 5.6 |
| −325 | 1.1 |

EXAMPLE 2

Using the same quantities of ingredients as in Example 1, the process is repeated but in this case the riboflavin is dispersed in the cyclohexane along with the ethylcellulose from the start. Under these conditions, the system becomes very viscous and large aggregated masses of encapsulated product are obtained. Essentially, the system is uncontrollable in terms of fluidity.

EXAMPLE 3

Using the process described in Example 2 but reducing the amount of ethylcellulose to 137 g. and the amount of riboflavin to 827 g., it is found that these decreased amounts are necessary to achieve proper fluidity. The resulting microcapsules consist of enrobed single crystals of riboflavin or enrobed agglomerates containing from 2 to 5 crystals. These capsules are all below the 50 micron range.

EXAMPLE 4

A dispersion of 32 g. of ethylcellulose (the same as used in Example 1) in 500 ml. of cyclohexane is heated to 78° C. while stirring with a double upthrust turbine at 330 RPM. The resulting mixture is cooled to 50° C. and 127 mg. of microatomized Indomethacin is added. The mixture is then heated to 60° C., cooled to −10° C., washed twice with 150 ml. of hexane and dried. The resulting microcapsules containing the Indomethacin are found to be in the 80 micron range.

EXAMPLE 5

A dispersion of 7.5 g. of ethylcellulose (the same as used in Example 1) and 5.4 g. of polyethylene granules having a molecular weight of about 7000 in 500 ml. of cyclohexane is heated to 78° C. while stirring with a double upthrust turbine at 240 RPM. At this temperature both the ethylcellulose and the polyethylene are dissolved in the cyclohexane. The stirring is continued while allowing the system to cool. As the temperature drops, solvated ethylcellulose develops as a separate phase due to the presence of polyethylene. As the temperature drops further, the ethylcellulose loses solvent and develops into semiplastic, dispersed, small masses. At 50° C. the cooling is discontinued and 67.5 g. of microatomized Indomethacin is added. Microscopic examination of the mixture at this point shows that the ethylcellulose is plastic enough for most of the Indomethacin to enter the masses and be enveloped. The temperature of the mixture is then raised to 58° C. and a microscopic examination at this point indicates that the Indomethacin is all enveloped. The mixture is then cooled to 10° C., washed twice with 150 ml. of hexane and dried. Examination of the resulting microcapsules show that they are in the 10 to 50 micron range.

EXAMPLE 6

Using the procedures described in Example 5 with 7.5 g. of ethylcellulose and 2.5 g. of polyethylene, 29.4 g. of Benzocaine is enveloped to afford microcapsules containing this product.

EXAMPLE 7

A dispersion of 24 g. of ethylcellulose of the same type as used in Example 1 in 500 ml. of cyclohexane is heated to 78° C. while stirring with a double upthrust impeller running at 240 RPM. The mixture is then cooled to 50° C. and 136 g. of ascorbic acid (30–80 mesh) is added. The mixture is then heated to 57° C., cooled to 10° C., and the solids are recovered by filtration. The filtered product is washed twice with 150 ml. of hexane and air dried. Microscopic examination of the resulting microcapsules shows that the products contain several ascorbic acid particles with walls of a thickness of 100 to 200 microns.

EXAMPLE 8

The process of Example 7 is repeated, but in this case the ascorbic acid is added at the very beginning along with the ethylcellulose. After heating to 78° C., the mixture is cooled directly to 10° C. and the resulting encapsulated product is recovered as described in the previous example. Microscopic examination of the resulting microcapsules show that they are of smaller size than the microcapsules obtained by the process of Example 7 and have walls of about 10 micron thickness.

EXAMPLE 9

A dispersion of 240 g. of ethylcellulose of the same type as used in Example 1, 898.6 g. of niacinamide, 215.4 g. of riboflavin and 245.9 g. of thiamine mononitrate in 5 liters of cyclohexane is stirred using two downthrust turbine impellers and baffles. A very high rate of stirring is required to maintain the material in suspension; the air driven motor being run at 545 RPM. The resulting mixture is heated to 76.5° C. and additional solvent is added to compensate for evaporative losses. The stirring is continued while the system is allowed to cool. The solvated ethylcellulose phases out and is distributed in the cyclohexane as droplets which tend to wet small clumps of the vitamin mixture and envelope them. As the temperature continues to drop, the ethylcellulose loses solvent and develops into solid encapsulating walls. At 58° C. the viscosity of the system decreases and at 49° C. the stirring is reduced to 341 RPM. The mixture is cooled further to 10° C., filtered, and the solids washed twice with 1.5 liters of hexane and dried in a fluid bed drier to yield microcapsules of the following mesh analysis:

| Sieve Size | % by Weight |
| --- | --- |
| +12 | 0.4 |
| −12/+16 | 1.4 |
| −16/+20 | 3.6 |
| −20/+30 | 9.4 |
| −30/+40 | 14.9 |
| −40/+60 | 30.1 |
| −60/+80 | 23.0 |
| −80+100 | 9.3 |
| −100/+140 | 5.2 |
| −140/+200 | 2.3 |
| −200/+325 | 0.4 |
| −325 | 0 |

EXAMPLE 10

The process described in Example 9 is repeated except that the riboflavin is not included in the initial dispersion. Thus, the ethylcellulose, niacinamide and thiamine in cyclohexane are heated to 78° C. with stirring at 465 RPM. This stirring is sufficient to insure thorough mixing of the ingredients. The batch is then cooled to 50° C. and the riboflavin is added over a period of 10 minutes. Microscopic examination of the mixture shows that the ethylcellulose is plastic enough for most of the riboflavin to enter the microcapsules. The temperature is then raised to 57° C., at which temperature all of the riboflavin is found to have entered the microcapsules. The mixture is then cooled to 10° C., washed with cyclohexane, and dried. The resulting microcapsules have the following mesh analysis:

| Sieve Size | % by Weight |
|---|---|
| +12 | 0.1 |
| −12/+16 | 0.9 |
| −16/+20 | 2.4 |
| −20/+30 | 4.7 |
| −30/+40 | 5.4 |
| −40/+60 | 9.9 |
| −60/+80 | 10.5 |
| −80/+100 | 14.5 |
| −100/+140 | 22.7 |
| −140/+200 | 21.8 |
| −200/+325 | 6.0 |
| −325 | 1.0 |

EXAMPLE 11

Using the procedures described in Example 10 except that the batch is not heated following the addition of the riboflavin at 50° C., the resulting microcapsules are recovered by filtration and then dried to afford product having the following sieve analysis:

| Sieve Size | % by Weight |
|---|---|
| 12 | — |
| −12/+16 | 0.2 |
| −16/+20 | 0.6 |
| −20/+30 | 1.2 |
| −30/+40 | 3.5 |
| −40/+60 | 23.6 |
| −60/+80 | 20.4 |
| −80/+100 | 14.0 |
| −100/+140 | 14.8 |
| −140/+200 | 13.9 |
| −200/+325 | 6.2 |
| −325 | 1.5 |

The microcapsules of Examples 9, 10 and 11 are evaluated by availability of riboflavin using release studies of the encapsulated riboflavin in simulated gastric fluid. These tests are carried out by mixing 50 mg. samples of the microcapsules with 150 ml. portions of simulated gastric fluid, T.S. (U.S.P.) and stirring the mixture at 38° C. overnight. At the indicated time intervals, the flasks are removed, diluted to 250 ml. with distilled water, shaken, and a 6 ml. sample is pipetted through glass wool into a 100 ml. volumetric flask containing 0.3 ml. of 0.1N hydrochloric acid. The flask is then diluted to the mark with distilled water and 5 ml. of this mixture is diluted to 50 ml. with 2% acetic acid. The resulting solution is read on a spectrofluorophotometer at 460 mμ exciter wavelength and 515 mμ analyzer wavelength for the amount of riboflavin released. The results are as follows:

| Sample (−40 mesh) | Time in Simulated Gastric Fluid (min.) | Riboflavin Released (%) |
|---|---|---|
| Microcapsules of Example 9 | 15 | 15.75 |
| | 30 | 29.14 |
| | 60 | 26.34 |
| | 120 | 43.27 |
| | 240 | 67.26 |
| Microcapsules of Example 10 | 15 | 34.89 |
| | 30 | 50.21 |
| | 60 | 55.89 |
| | 120 | 77.45 |
| | 240 | 86.38 |
| Microcapsules of Example 11 | 15 | 81.30 |
| | 30 | 106.42 (?) |
| | 60 | 96.12 |
| | 120 | 98.66 |
| | 240 | 99.36 |

The above results indicate that when the riboflavin is added at 57° C. as in Example 10, the riboflavin is more readily extracted than when it had been added along with the initial ingredients as described in Example 9. It appears likely that this is due to the riboflavin of Example 10 being closer to the periphery of the microcapsules than it is when prepared by the process of Example 9. The tabulated results also clearly show that when the riboflavin is added at 50° C. as described in Example 11, it is still more readily available.

EXAMPLE 12

An 11% solution of 250 Bloom porkskin gelatin in distilled water was prepared (I) and held at 55° C. An 11% solution of gum Arabic in distilled water was prepared (II) and held at 55° C.

90 Ml. of (I), 90 ml. of (II) and 350 ml. distilled water (previously warmed to 55° C.) were blended and kept stirring with a flat bladed impeller. Microscopic examination of this blend (III) showed an essentially clear liquid. The pH of (III) was adjusted to 4.5 with 10% aqueous acetic acid. Microscopic examination now showed a rich dispersion of the highly hydrated protein-gum complex was kept stirring, and allowed to cool to 40° C. The system was allowed to cool slowly. At 38° C. microscopic examination showed that coacervate droplets were wetting each other to form spheres. At that temperature, 54 gm. of Indomethacin was added. Cooling was continued. At 25° C. there were discrete microcapsules of aggregated Indomethacin particles. This system was chilled to 10° C. and 4.5 ml. of 25% aqueous glutaraldehyde was added to crosslink the capsular wall material. The system was allowed to stir overnight. The capsules were washed with chilled, distilled water and air dried.

EXAMPLE 13

Riboflavin was microencapsulated using the process as taught in Balassa U.S. Pat. No. 3,495,988, modified to use their invention.

A 36% aqueous solution of gelatin was brought to 40° C. with stirring. This was added with stirring to 600 gm. white mineral oil. The white mineral oil was at 40° C. 50 Gm. Riboflavin Superfine Powder (Merck Type 59921) was then added with stirring, keeping the temperature of the system at 40° C. The resultant System II was a slurry of gel in mineral oil, the gel entraining riboflavin. The slurry particle size was about 100μ.

System II was poured with stirring into 3 liters of 95% ethanol previously adjusted to 20° C. The System III was allowed to stir for an hour to allow dehydration of the spheres. Liquid was decanted. The spheres were washed with 95% aqueous ethanol at 20° C. and spread to dry.

We claim:

1. A process for producing microencapsulated solid products which comprises introducing said solid products in a finely divided state to soft blank microcapsules formed from an encapsulating material selected from the group consisting of ethylcellulose, methylcellulose, hydroxypropylmethylcellulose, polyvinyl alcohol, cellulose acetate phthallate, gelatin, gum arabic and carageenan alginates in a solvent medium, hardening said soft microcapsules after said solid products have entered said microcapsules, and recovering the microencapsulated product from the resultant mixture.

2. A process for producing ethylcellulose encapsulated product which comprises heating a dispersion of ethylcellulose in cyclohexane to effect a solution of said ethylcellulose; then cooling the resultant solution to obtain a dispersion of finely divided ethylcellulose capsules, adding a solid product to the soft ethylcellulose capsules at a temperature between 45° C. and 60° C. and agitating the resulting mix for sufficient time to envelope the added solid product.

3. The process of claim 2 in which the solid product is a medicament.

4. The process of claim 2 in which the solid product is a vitamin.

5. The process of claim 4 in which the vitamin is riboflavin.

6. In the process of microencapsulation, the step which comprises adding the solid product to be microencapsulated to a suspension of heat softened blank microcapsules formed from an encapsulating material selected from the group consisting of ethylcellulose, methylcellulose, hydroxypropylmethylcellulose, polyvinyl alcohol, cellulose acetate phthallate, gelatin, gum arabic and carageenan alginates.

* * * * *